US010336598B2

(12) United States Patent
Cronin et al.

(10) Patent No.: US 10,336,598 B2
(45) Date of Patent: Jul. 2, 2019

(54) PORTABLE, POD-BASED SMOOTHIE MAKER

(71) Applicant: Jooster IP AG, Bielbenken BL (CH)

(72) Inventors: John Cronin, Bonita Springs, FL (US); Steven Matthew Philbin, Livermoore, CA (US)

(73) Assignee: Jooster IP AG, BielBenken BL (CH)

( * ) Notice: Subject to any disclaimer, the term of this patent is extended or adjusted under 35 U.S.C. 154(b) by 0 days.

(21) Appl. No.: 16/105,692

(22) Filed: Aug. 20, 2018

(65) Prior Publication Data

US 2018/0352999 A1   Dec. 13, 2018

Related U.S. Application Data

(63) Continuation of application No. PCT/US2017/018463, filed on Feb. 17, 2017.
(Continued)

(51) Int. Cl.
*A47J 31/40* (2006.01)
*B67D 1/00* (2006.01)
*B65D 51/28* (2006.01)
*A47J 31/00* (2006.01)
*B65D 25/08* (2006.01)
(Continued)

(52) U.S. Cl.
CPC .............. *B67D 1/0078* (2013.01); *A23L 2/52* (2013.01); *A47J 31/005* (2013.01); *A47J 31/401* (2013.01); *A47J 31/404* (2013.01); *A47J 31/407* (2013.01); *B65D 25/08* (2013.01); *B65D 51/2807* (2013.01); *B67D 1/00* (2013.01); *B67D 1/0021* (2013.01); *F25D 23/126* (2013.01); *F25D 29/00* (2013.01); *F25D 2400/361* (2013.01)

(58) Field of Classification Search
CPC .... A47J 31/005; A47J 31/0673; A47J 31/401; A47J 31/402; A47J 31/404; A47J 31/407; B65D 51/2807; B65D 25/08; B65D 81/3266
USPC ........ 99/323, 289 R, 291, 295; 206/0.5, 222, 206/219, 221; 222/83, 83.5, 144
See application file for complete search history.

(56) References Cited

U.S. PATENT DOCUMENTS 7,681,726 B2 *  3/2010  O'Donnell ......... B65D 51/2828
                                                        206/222
8,875,751 B1 * 11/2014  Nueman, Jr. ........... A47J 47/04
                                                        141/104
(Continued)

FOREIGN PATENT DOCUMENTS

JP       63-062340 U      4/1988
KR    10-2014-0083585 A   7/2014
WO      2017/143251 A1    8/2017

OTHER PUBLICATIONS

Korean Intellectual Property Office, International Search Report for PCT Application No. PCT/US2017/018463, dated May 31, 2017.
(Continued)

*Primary Examiner* — Reginald Alexander
(74) *Attorney, Agent, or Firm* — Socal IP Law Group LLP; Nikki M. Dossman; Steven C. Sereboff

(57) ABSTRACT

The apparatuses described herein provide a portable, pod-based beverage maker, such as an apparatus that makes smoothies and other similar beverages from pod-based ingredient mixtures. The apparatus provides an easy and simple way to combine ingredients in pods with water, ice, and other mixing liquids.

18 Claims, 5 Drawing Sheets

Related U.S. Application Data

(60) Provisional application No. 62/297,632, filed on Feb. 19, 2016, provisional application No. 62/297,644, filed on Feb. 19, 2016, provisional application No. 62/296,851, filed on Feb. 18, 2016, provisional application No. 62/297,716, filed on Feb. 19, 2016, provisional application No. 62/296,814, filed on Feb. 18, 2016, provisional application No. 62/296,844, filed on Feb. 18, 2016, provisional application No. 62/297,711, filed on Feb. 19, 2016, provisional application No. 62/297,009, filed on Feb. 18, 2016.

(51) Int. Cl.
*A23L 2/52* (2006.01)
*F25D 29/00* (2006.01)
*F25D 23/12* (2006.01)

(56) References Cited

U.S. PATENT DOCUMENTS

| | | |
|---|---|---|
| 2004/0007481 A1 | 1/2004 | Kiser, Jr. |
| 2005/0284302 A1 | 12/2005 | Levin |
| 2006/0071000 A1 | 4/2006 | Weist et al. |
| 2006/0226035 A1* | 10/2006 | Smith .................... B65D 25/08 206/219 |
| 2011/0089059 A1* | 4/2011 | Lane ...................... B65D 47/08 206/222 |
| 2013/0001111 A1* | 1/2013 | Knutsen .................... A45F 3/18 206/222 |
| 2018/0178957 A1* | 6/2018 | Zalewski ........... B65D 51/2835 |

OTHER PUBLICATIONS

Korean Intellectual Property Office, Written Opinion of the International Searching Authority for PCT Application No. PCT/US2017/018463, dated May 31, 2017.

\* cited by examiner

PORTABLE, POD-BASED SMOOTHIE MAKER

CROSS-REFERENCE TO RELATED APPLICATION(S)

This application is a bypass continuation of Patent Cooperation Treaty Application No.: PCT/US2017/018463, filed on Feb. 17, 2017, entitled "PORTABLE, POD-BASED SMOOTHIE MAKER", which claims priority to the following U.S. Provisional Patent Applications: U.S. Provisional Patent Application No. 62/296,814 filed on Feb. 18, 2016, entitled "PROVIDING A USER INTERFACE FOR CUSTOMIZING BEVERAGE PROFILES;" U.S. Provisional Patent Application No. 62/296,844 filed on Feb. 18, 2016, entitled "REFRIGERATOR WITH POD-BASED BEVERAGE DISPENSER;" U.S. Provisional Patent Application No. 62/296,851 filed Feb. 18, 2016, entitled "CUSTOMIZING BEVERAGE PROFILES TO USER SLEEP CYCLES;" U.S. Provisional Patent Application No. 62/297,009 filed Feb. 18, 2016, entitled "RECOMMENDING MODIFICATIONS TO USER-CREATED BEVERAGE PROFILES;" U.S. Provisional Patent Application No. 62/297,644 filed Feb. 19, 2016, entitled "CUSTOMIZING BEVERAGE PROFILES TO USER MENTAL ACUITY;" U.S. Provisional Patent Application No. 62/297,711 filed Feb. 19, 2016, entitled "PORTABLE, POD-BASED SMOOTHIE MAKER;" U.S. Provisional Patent Application No. 62/297,716 filed Feb. 19, 2016, entitled "CUSTOMIZING BEVERAGE PROFILES TO USER WELLNESS PROGRAMS;" and U.S. Provisional Patent Application No. 62/297,632 filed Feb. 19, 2016, entitled "CUSTOMIZING BEVERAGE PROFILES TO USER ACTIVITIES;" each of which are hereby incorporated by reference in their entirety.

BACKGROUND

There are numerous retailers, distributors, and companies that attempt to target users with supplements, beverages, and other nutritional foods or drinks. However, most of these products are pre-made and generic to a certain population of users and/or for a certain purpose. For example, companies create sports drinks to assist the performance of a generic user during activities, and retailers sell smoothies that promote certain health benefits to a large population of users.

DETAILED DESCRIPTION

Figure 1:
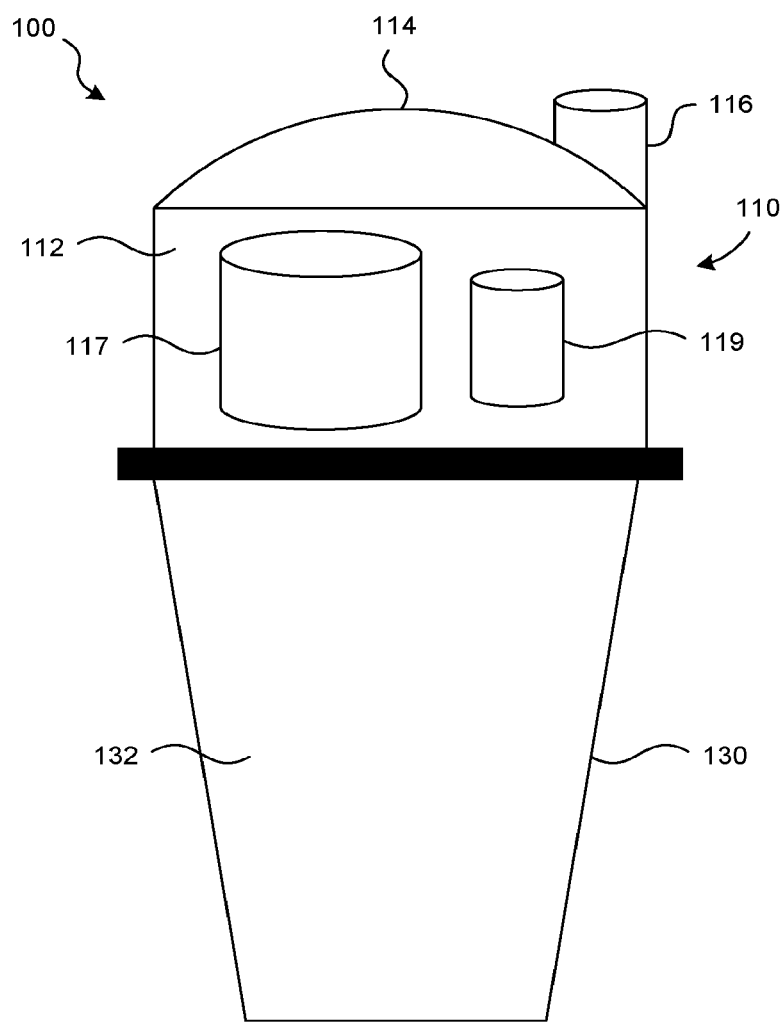
FIG. 1 is a diagram showing a side view of a beverage maker configured in accordance with the present technology.

The apparatuses described herein provide a portable, pod-based beverage maker, such as an apparatus that makes smoothies and other similar beverages from pod-based ingredient mixtures. The apparatus provides an easy and simple way to combine ingredients in pods with water, ice, and other mixing liquids.

For example, the beverage maker may receive one or more pods above a larger container or vessel such as a plastic cup for use by a user. The beverage maker can further include components that allow a user to twist a carousel through a number of positions in order to selectively add beverage ingredients to the container. For example, a user turns the carousel though a set of positions, where at each position the carousel "clicks" into place. In a first position, one or more pods are loaded into the beverage maker while being shielded from an inner area of the container. In a second position, at least one of the pods may be opened and its contents can enter the inner area while being shielded from liquid, thereby allowing the beverage maker to be carried around without fear of any spoilage since a consumable beverage has yet to be created. Thereafter, a liquid opening is exposed by rotating the carousel to a third position, and the container is filled with liquid. Once filled, the pods and a liquid inlet are both shielded from the beverage by rotating the carousel back to the first position, and a user can handshake the beverage maker to create a consumable beverage without spilling the contents. In some embodiments the carousel can have one or more additional positions. For example, in certain embodiments, the user can rotate the carousel to an additional position between the second and third positions. In this additional position, the liquid inlet and pods are fully shielded from the inner area of the container. Accordingly, contents from the one or more pods cannot reenter the previously emptied pods while a user carries or otherwise transports the beverage maker.

The beverage pods, or smoothie pods, may be pods or cartridges containing specific mixtures of ingredients. For example, a pod may include a mixture of various freeze dried fruits (e.g., freeze dried bananas, strawberries, blueberries, mango, etc.), freeze dried vegetables (e.g., kale, spinach, beets, etc.), additive powders (e.g., protein powders, powdered greens, oils, seeds, supplements, flavors, etc.). In some cases, a pod may include a mixture of many different ingredients. In other cases, the pod may include one or more ingredients.

In the following description, for the purposes of explanation, numerous specific details are set forth in order to provide a thorough understanding of embodiments of the present technology. It will be apparent to one skilled in the art, however, that embodiments of the present technology may be practiced without some of these specific details.

The terminology used herein is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

Further details regarding the systems, devices, methods, and routines will be described herein. The figures have not necessarily been drawn to scale. Similarly, some components and/or operations may be separated or combined for the purposes of discussion of some of the embodiments of the present technology. Moreover, while the technology is amenable to various modifications and alternative forms, specific embodiments have been shown by way of example in the figures and are described in detail below. The intention, however, is not to limit the technology to the particular embodiments described. On the contrary, the technology is intended to cover all modifications, equivalents, and alternatives falling within the scope of the technology as defined by the appended claims.

FIG. 1 is a side view of a beverage maker 100 in accordance with some embodiments of the present technology. As illustrated, the beverage maker 100 includes a carousel 120 positioned between top 110 and container bottom 130. The bottom 130 may be configured as a bottle, cup, or other similar container, typically sized to be held in one hand by a user. In some embodiments, the carousel 120 is permanently coupled to pod holder 112 or another portion of the top 110. The carousel 120 and top 110 can therefore form a cap structure that can be configured for attachment to any type of container bottom 130. In other embodiments, the carousel 120 is a separate component of beverage maker 100 that can be removed from the top portion 110. One advantage of providing the carousel 120 as a separable component from the top 110 is that it can make cleaning the beverage maker 100 easier. That is, a user can separate and wash the carousel 120 along with the bottom 130 without having to wash the top 110—which in some embodiments is not exposed to the created beverage. In yet other embodiments, the carousel 120 can be adjustably positionable within or above the container bottom 130. For example, the carousel 120 can be lowered into the inner area 132 of the container bottom 130 in order to reduce the volume of the inner area 132 (e.g., in order to make a smaller consumable beverage).

Top 110 further includes pod holder 112, lid 114, and liquid fill inlet 116. Liquid fill inlet 116 is configured to receive a liquid therethrough. Pod holder 112 is configured to receive at least one pod containing beverage contents. Specifically, pods can be inserted into the pod holder 112 when the lid 114 has been removed. In some embodiments, once pods are inserted into the pod holder 112, the lid 114 secures the pods against carousel 120. In certain embodiments, the lid 114 is detachable from the top 110. In other embodiments, the lid 114 can pivot, swing, or otherwise move to provide access to the pod receptacles 117 and 119.

In the illustrated embodiment, pod holder 112 includes primary pod receptacle 117 and supplemental pod receptacle 119. Primary pod receptacle 117 can receive, for example, a larger pod containing freeze dried fruits and/or vegetables. Supplemental pod receptacle 119 can receive, for example, a smaller pod containing additive powders, oils, seeds, supplements, flavors, etc. In other embodiments, the pod holder 112 contains a single pod receptacle, or more than two pod receptacles.

Carousel 120 is rotatable and is generally configured to provide selective access to an inner area 132 of container bottom 130 from the top 110. More specifically, carousel 120 can include one or more pod openings and a liquid opening that provide access to the inner area 132 of container bottom 130. The openings are selectively shielded from pod receptacles 117 and 119 and liquid fill inlet 116 depending on the position of the carousel 120.

FIGS. 2-5 illustrate cross-sectional side views of the carousel 120 and top 110 of the beverage maker 100 shown in FIG. 1. In particular, FIGS. 2-5 show the carousel 120 in different positions that provide varying degrees of access to the container bottom 130 (not pictured) from the top 110. In the illustrated embodiments, carousel 120 includes primary pod opening 202, supplemental pod opening 204, and liquid opening 206, all extending through the carousel 120 and positioned above the container bottom 130 to provide access between the top 110 and container bottom 130. Primary pod opening 202 is aligned along a common axis with primary pod receptacle 117, supplemental pod opening 204 is aligned along a common axis with supplemental pod receptacle 119, and liquid opening 206 is aligned along a common axis with liquid fill inlet 116. In certain embodiments, the carousel 120 includes more or fewer openings depending on the number of pod receptacles included in the pod holder 112. For example, if the pod holder 112 includes only one primary pod receptacle 117, the carousel can have only a single corresponding opening 202 and no supplemental pod opening 204.

According to the present technology, the carousel 120 can generally be twisted or rotated through one or more positions that provide the top 110 with varying access to the inner area 132 of container bottom 130. For example, as described in detail below, a user can twist the carousel 120 in order to rotate a series of grommet blanks, grommets, and pod openers relative to the fixed top 110 and openings 202, 204, and 206. In some embodiments, the carousel 120 includes a locking mechanism that locks the carousel 120 in place at each of the one or more positions. For example, the carousel 120 can include a series of grooves and corresponding inserts that fit together at each position. By applying more rotational force to the carousel 120, the user can overcome the locking mechanism and move the beverage maker 100 to another position. In certain embodiments, the carousel 120 further includes a mechanism that permits the carousel 120 to rotate in only a single direction (e.g., in the counterclockwise direction). In other embodiments, the carousel 120 is rotatable in either direction such that the user can rotate the carousel 120 back-and-forth between adjacent positions.

Figure 2:
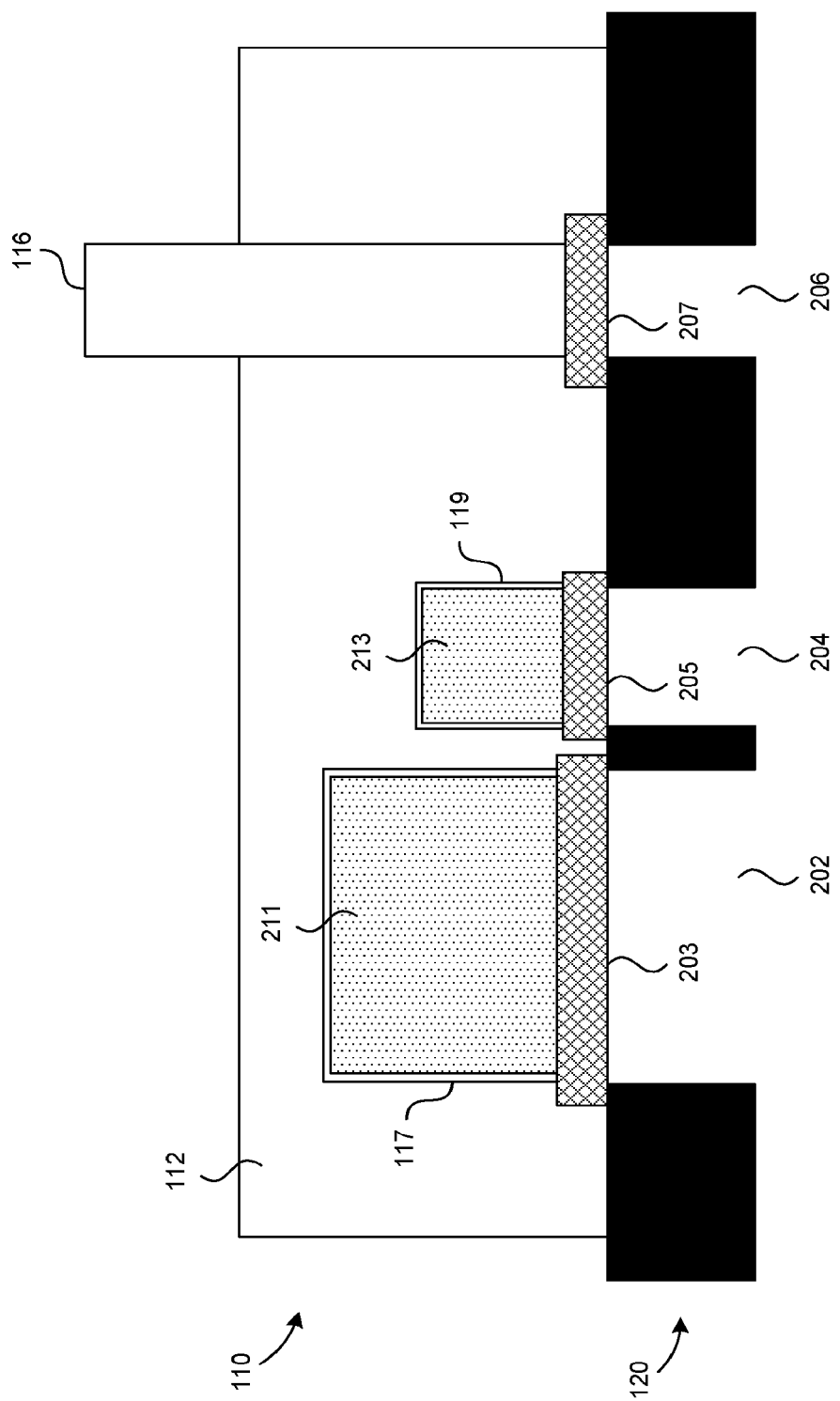
FIG. 2 is a cross-sectional side view of a top portion of the beverage maker shown in FIG. 1, and showing a carousel of the beverage maker in a first position.

FIG. 2 shows the top 110 with the lid 114 removed so that primary pod 211 can be inserted in the primary pod receptacle 117 and supplemental pod 213 can be inserted into supplemental pod receptacle 119. As illustrated, the pods 211 and 213 contain beverage contents when they are inserted. The carousel 120 is in a first position. In the first position, grommet blanks 203, 205, and 207 block the primary pod opening 202, supplemental pod opening 204, and liquid opening 206, respectively. The top 110—and specifically the pod receptacles 117 and 119 and liquid fill inlet 116—are therefore shielded from the inner area 132 of bottom 130. The grommet blanks 203, 205, and 207 can be made of rubber or other waterproof materials.

In some embodiments, the pods 211 and 213 are positioned on the grommet blanks 203 and 205. In such embodiments, the lid 114 can be attached to the top 110 and can engage a top portion of the pods 211 and 213 to secure the pods in place against the grommet blanks 203 and 205. In other embodiments, the pods 211 and 213 are positioned slightly above the grommet blanks 203 and 205. For example, an internal structure within the pod receptacles 117 and 119—such as one or more struts—can keep the pods 211 and 213 from being supported by only the rubber grommet blanks 203 and 205. In yet other embodiments, the pods 211 and 213 can include a flange or other structure that supports the pods 211 and 213 within the receptacles 117 and 119. For example, pods 211 and 213 can have an upper portion including a flange that is configured to extend outside the receptacles 117 and 119 to support the pods 211 and 213 via an upper surface of the receptacles 117 and 119. In still other embodiments, the pods 211 and 213 are shaped to engage an inner surface of the pod receptacles 117 and 119 and are therefore seated within the receptacles 117 and 119.

Figure 3:
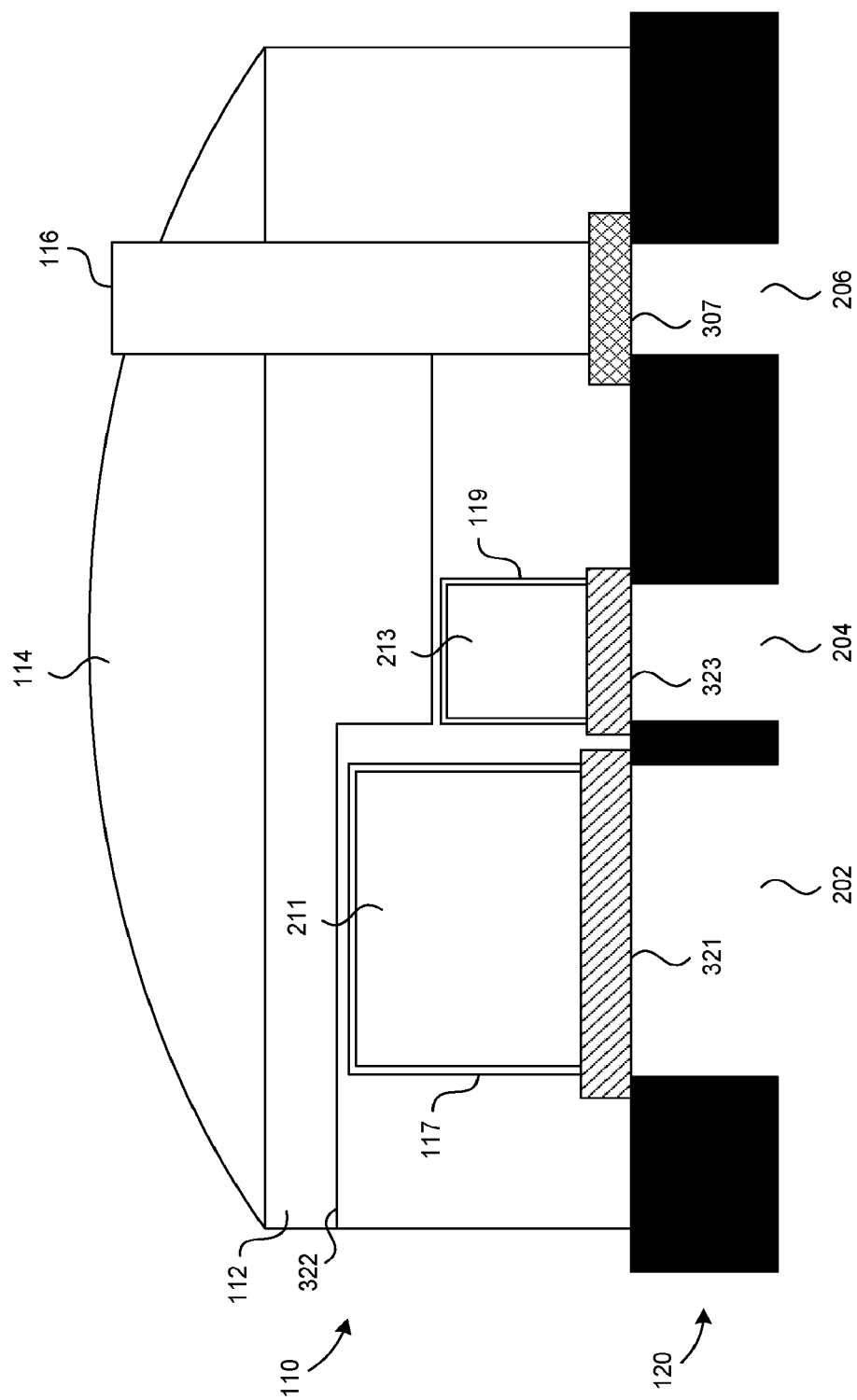
FIG. 3 is a cross-sectional side view of a top portion of the beverage maker shown in FIG. 1, and showing the carousel in a second position.

FIG. 3 shows the carousel 120 in a second position. In the second position, a bottom surface of the primary pod 211 and a bottom surface of supplemental pod 213 are cut open to permit contents within the pods 211 and 213 to move to the inner area 132 of the container bottom 130. As illustrated, the pods 211 and 213 are emptied of their contents in the second position. A grommet blank 307 blocks the liquid opening 206 so that the liquid fill inlet 116 is shielded from the inner area 132 of the container bottom 130. The carousel 120 includes primary pod opener 321 and supplemental pod opener 323 that comprise one or more cutting elements. The cutting elements may include, for example, a plurality of small pins, a cutting edge, or other device configured to cut, pierce or otherwise penetrate a bottom surface of pods 211 and 213. In certain embodiments, the pods have a foil or plastic bottom surface which is cut open to allow the pod contents to fall into the container bottom 130 through pod openings 202 and 204.

In some embodiments, the pod openers 321 and 323 operate to open the pods 211 and 213 when the carousel is turned from the first position to the second position. That is, rotating the carousel from the first position to the second position causes the openers 321 and 323 to engage the bottom surfaces of pods 211 and 213, respectively, to permit the pod contents to move to the container bottom 130. A bottom surface 322 of lid 114 can engage top portions of the pods 211 and 213 to secure the pods 211 and 213 against the pod openers 321 and 323 while the carousel 120 is rotated from the first position to the second position. The pod openers 321 and 323 can include openings or space between cutting elements to allow the pod contents to fall through the pod openers 321 and 323 and into the container bottom 130. In other embodiments, the pod openers 321 and 323 are only aligned with the pods 211 and 213 as the carousel is twisted from the first to the second position. Then, in the second position, the pods 211 and 213 are directly above the primary pod opening 202 and supplemental pod opening 204 to allow the contents of the pods 211 and 213 to fall into the container bottom 130 (i.e., the contents does not pass through the pod openers 321 and 323 to enter to the container bottom 130).

Figure 4:
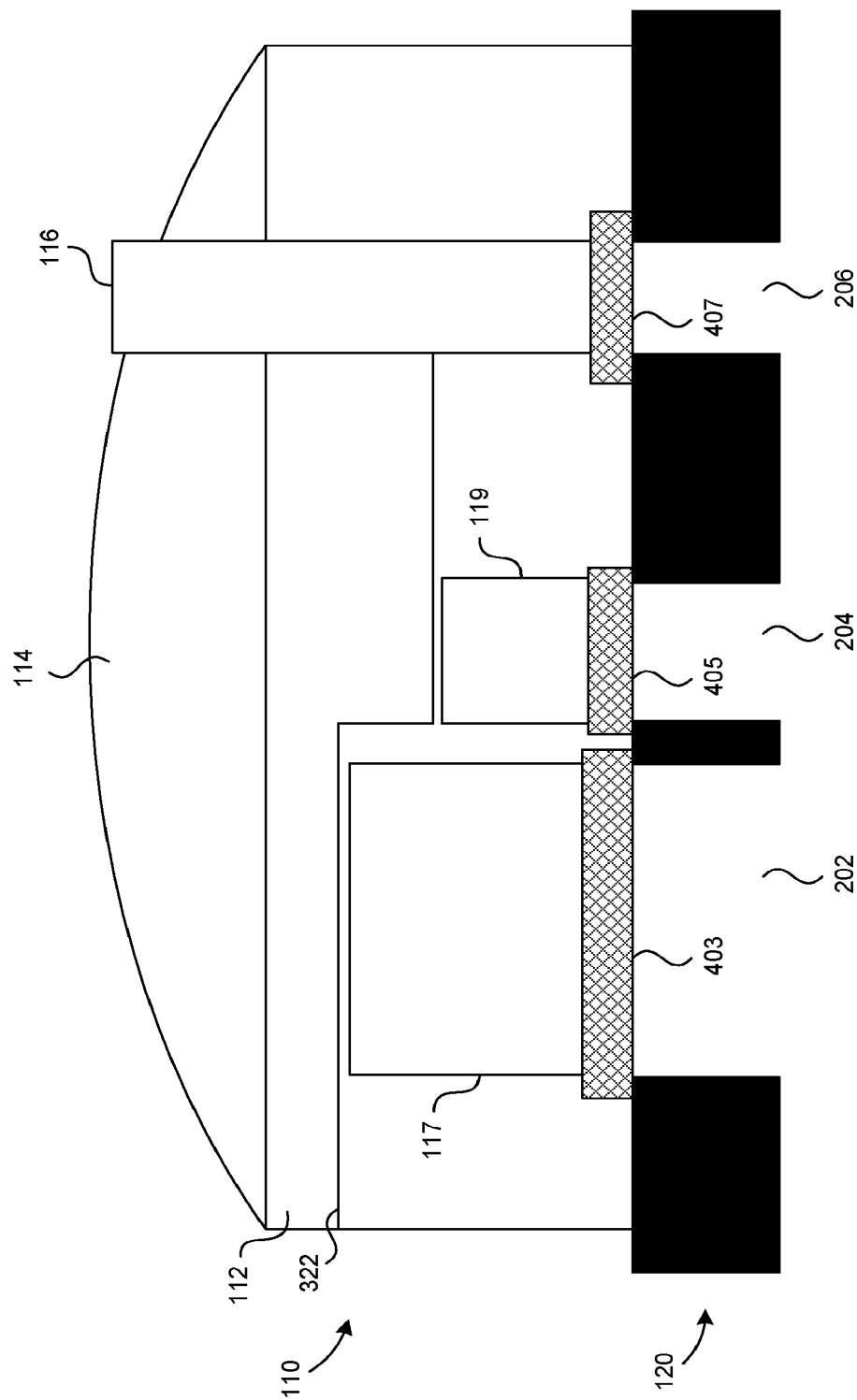
FIG. 4 is a cross-sectional side view of a top portion of the beverage maker shown in FIG. 1, and showing the carousel in an optional third position.

FIG. 4 shows the carousel in an optional third position. The third position is similar to the first position in that grommet blanks 403, 405, and 407 block the primary pod opening 202, supplemental pod opening 204, and liquid opening 206, respectively. The top 110 is therefore entirely shielded from the inner area 132 of container bottom 110. The optional third position permits the user to detach or move the lid 114 from the top 110 and to remove the emptied primary pod 211 and supplemental pod 213. As illustrated, the pods 211 and 213 have been removed from the receptacles 117 and 119 and the top 114 has subsequently been replaced. This optional third position also permits a user to carry or transport the beverage maker 100 without backflow of the pod contents into the emptied pods 211 and 213. For example, if transported in the optional third position, the beverage maker 100 will prevent backflow of the pod contents into the top 110 if the beverage maker is inverted or otherwise jostled.

Figure 5:
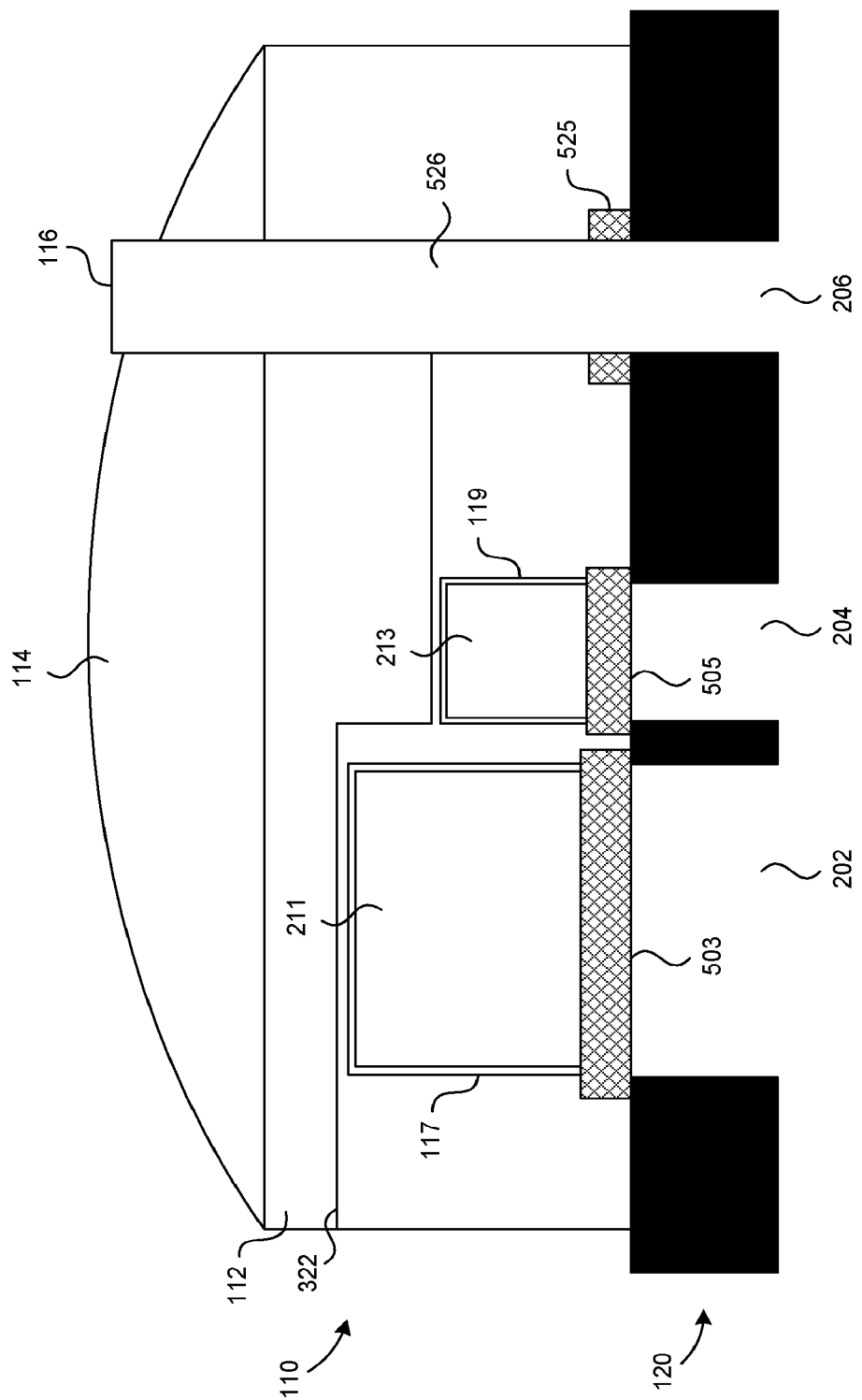
FIG. 5 is a cross-sectional side view of a top portion of the beverage maker shown in FIG. 1, and showing the carousel in a fourth position.

FIG. 5 shows the carousel 120 in a fourth position. The emptied pods 211 and 213 have yet to be removed from the top 110 (e.g., removed in the optional third position.) In the fourth position, the liquid opening 206 is exposed to the fill inlet 116, while grommet blanks 503 and 505 block the primary pod opening 202 and supplemental pod opening 204, respectively. The liquid fill inlet 116 and liquid opening 206 together define a channel 526 through which liquid can flow from the top 110 and into the container bottom 130. Water, other liquids, or both, can therefore be added to into the beverage maker 100 while the pods 211 and 213 are shielded from the container bottom 130. In certain embodiments, the carousel 120 includes liquid grommet 525 positioned between the fill inlet 116 and liquid opening 206. Liquid grommet 425 further defines the channel 526 and functions to seal the channel 526 in order to prevent liquid from leaking into other portions of the top 110.

Now described, with reference to FIGS. 1-5, is an exemplary method of using a beverage maker 100 configured in accordance with the present technology to create a consumable beverage. To begin, while the carousel is in the first position, the lid 114 is removed and one or more pods (e.g., primary pod 211 and supplemental pod 213) are inserted into corresponding receptacles in the top 110 (e.g., primary pod receptacle 117 and supplemental pod receptacle 119). The lid 114 is then reattached to the top 110 in order to secure the pods against grommet blanks 203 and 205 in the carousel.

Next, the user twists the carousel 120 by hand from the first position to the second position to release the contents of pods 211 and 213 into the inner area 132 of the container bottom 130. In some embodiments, the user can then twist the carousel 120 to the optional third position. In the optional third position, the user can remove the lid 114 and the pods 211 and 213. The user may also transport the beverage maker 100 in the third position—including inverting the beverage maker 100—without fear of the contents reflowing into the top 110. The user also need not worry about spoiling, since a consumable beverage including liquid has yet to be created. Thereafter, the user may rotate the carousel 120 to the fourth position and fill the container bottom 130 with liquid via fill inlet 116. Finally, the carousel 120 may be rotated back to the first position and the beverage maker 100 shaken to create a consumable beverage such as a smoothie. Alternatively, the carousel 120 can be rotated back to the optional third position and the beverage maker 100 shaken in the third position.

In some embodiments, the carousel 120 is configured such that a single full rotation in one direction (e.g., the counterclockwise direction) will cause the carousel 120 to pass through each of the first through fourth positions. In other embodiments, the carousel 120 may require more or fewer rotations in order to pass through each position. Moreover, in certain embodiments, the carousel 120 is configured such that it can only be rotated sequentially through the different positions. For example, the carousel 120 may be configured to rotate only in the counterclockwise direction such that the first through fourth positions can only be accessed in numerical order. In still other embodiments, the carousel 120 is freely rotatable through the different positions in any order.

Of course, other variations of the beverage maker 100, including other components, geometries, and/or configurations, may be utilized. For example, instead of rotating a series of grommet blanks, grommets, and pod openers relative to the fixed top 110 and openings 202, 204, and 206, the top 110 could be rotated relative to the openings 202, 204, and 206. That is, the pods 211 and 213 could be rotated relative to the carousel 120 and the openings 202, 204, and 206 formed therein, to achieve functionally similar positions as those described above. Alternatively, the openings 202, 204, and 206 in carousel 120 could be rotated relative to fixed pods 211 and 213 to achieve similar positions.

As another example, the beverage maker 100 may include an accelerometer that tracks the shaking of the bottle, where the data is communicated to a user device (e.g., smartphone). Based on the accelerometer data, a number of calories burned can be calculated. Additionally, the accelerometer data could be used to determine when the beverage maker 100 has been shaken a sufficient amount. Once the sufficient amount has been reached, the user device could alert the user with haptic feedback or an auditory alert. In certain embodiments, the beverage maker 100 includes an accelerometer, a communications component, and a microprocessor coupled to the accelerometer and the communications component to track shaking of the beverage maker 100 and transmit data reflecting the shaking to a smartphone.

As another example, pods (e.g., pods 211 and 213) are opened immediately upon or soon after placement by the user within the beverage maker 100, and the contents are dumped into a separate compartment. The compartment is then opened by turning the carousel 120, allowing the contents to enter the container bottom 130. The compartment is then closed off by further turning the carousel 120. This allows the user to immediately dispose of the pods, and would allow for a smaller form factor for the beverage maker 100, among other things.

As another example, the beverage maker 100 may include an insulated compartment for storing ice. In some embodiments, the compartment is configured to be separate from, but adjacent to, the inner area 132 of container bottom 130 so as to keep the inner area 132 cool. In other embodiments, the compartment could be opened to allow the ice to enter the container bottom 130. The ice could either be in cube form to help keep the beverage cool for longer, or the ice could be crushed in order to give the smoothie a more traditional consistency.

As another example, the carousel 120 of beverage maker 100 may be adjustable in the vertical direction. This would allow the user to manually set a limit for the amount of liquid to be added to the container bottom 130. Once the liquid has been added, the carousel 120 can be adjusted upwards to allow for extra room in the inner area 132 of container bottom 130 to aid in the shaking process. In some embodiments, the carousel 120 is lowered vertically to a liquid-fill position within the container bottom 130 when the carousel 120 is in the fourth position. The carousel 120 is raised vertically to a shaking position when the carousel 120 is in either the optional third position or in the first position to facilitate the shaking process. A volume of the inner area 132 is greater when the carousel 120 is in the shaking position than when the carousel is in the liquid-fill position.

As another example, a vibrator in the carousel 120 may be activated when the carousel 120 is in the second position. The vibrator may assist in the release of powders or other contents from the pods, ensuring that the entirety of the pods' contents enter the container bottom 130 to be included in the beverage. The vibrator can turn off once the carousel 120 rotates to another position. In some embodiments, the one or more pods are smoothie pods, and beverage maker 100 includes a vibrator that activates only when the carousel 120 is in the second position to assist in the release of smoothie contents from the pods into the container bottom 130.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes are presented in a given order, alternative implementations may perform routines having steps in a different order, and some processes be deleted, moved, added, subdivided, combined, and/or modified to provide alternative or subcombinations. Each of these processes may be implemented in a variety of different ways. Also, while processes are at times shown as being performed in series, these processes may instead be performed or implemented in parallel, or may be performed at different times.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

We claim:

1. An apparatus for carrying a human-consumable liquid, the apparatus comprising:
    a container having an inner area, wherein the container is sized to be held in the hand of a user;
    a liquid inlet configured to receive liquid;
    a pod holder positioned above the inner area and configured to receive and hold one or more pods, wherein the one or more pods carry contents to be mixable with the liquid; and
    a carousel positioned between the inner area and the pod holder, wherein the carousel has a pod opening and a liquid opening, and wherein the carousel is selectively rotatable between at least a first position, a second position, and a third position, wherein:
        in the first position, the carousel shields the pod holder and the liquid inlet from the inner area,
        in the second position, the contents of a pod held in the pod holder move to the inner area of the container, and
        in the third position, the carousel shields the pod holder from the inner area and provides a channel from the liquid inlet, through the liquid opening, and to the inner area to permit a liquid received through the liquid inlet to mix with the pod contents in the inner area.

2. The apparatus of claim 1, further comprising a pod opener configured to open the pod inserted into the pod holder.

3. The apparatus of claim 2 wherein, in the second position, the pod inserted into the pod holder is opened by the pod opener.

4. The apparatus of claim 2 wherein the pod opener opens the pod inserted into the pod holder when the carousel is rotated to the second position from another position, and wherein the pod opener employs a cutting element to cut a portion of the pod.

5. The apparatus of claim 1 wherein the pod holder is configured to receive the one or more pods while the carousel is in the first position, and wherein the carousel is only selectively rotatable from (a) the first position to the second position, (b) the second position to the third position, and (c) the third position to the first position.

6. The apparatus of claim 1 wherein the carousel is selectively rotatable to a fourth position that shields the pod holder and the liquid inlet from the inner area.

7. The apparatus of claim 6 wherein the carousel is only selectively rotatable from (a) the first position to the second position, (b) the second position to the fourth position, (c) the fourth position to the third position, and (d) the third position to the first position.

8. The apparatus of claim 1 wherein the carousel is configured to be adjustably positionable within the container to thereby change a volume of the inner area, wherein: in the first position, the carousel is in a shaking position within the container, in the third position, the carousel is in a liquid-fill position within the container, and the volume of the inner area is larger when the carousel is in the shaking position than when the carousel is in the liquid-fill position.

9. The apparatus of claim 1 wherein the one or more pods are smoothie pods.

10. The apparatus of claim 1, further comprising a top structure configured to cover a top portion of the pod holder that is opposite the carousel.

11. The apparatus of claim 10 wherein the top structure is configured to secure a pod inserted into the pod holder in at least one of the first position, second position, and third position.

12. The apparatus of claim 11 wherein the top structure secures the pod against the carousel, and wherein the apparatus include an insulated compartment for holding ice or a frozen substance, wherein the compartment is configured to be separate from, but adjacent to, the inner area so as to keep the inner area cool.

13. The apparatus of claim 1 wherein the carousel provides a seal that prevents liquid and/or contents of a pod from leaving the inner area in the first position.

14. An apparatus, comprising:
    a container having an inner area;
    a liquid inlet configured to introduce liquid to the inner area of the container;
    a smoothie pod holder positioned above the inner area and configured to receive one or more smoothie pods; and
    a smoothie pod opener configured to open a smoothie pod inserted into the smoothie pod holder, wherein the smoothie pod holder includes a pod carousel rotatable to be selectively positionable proximate to a smoothie pod opening and to a liquid opening, and wherein the pod carousel is configured to rotate to various positions, including:
        a first position that shields the smoothie pod holder and the liquid inlet from the inner area;
        a second position, wherein the smoothie pod inserted into the smoothie pod holder is opened by the pod opener and contents of the smoothie pod moves to the inner area of the container in the second position; and
        a third position that shields the smoothie pod holder from the inner area and provides a channel from the liquid inlet, through the liquid opening, and to the inner area.

15. A cap for attachment to a container having an inner area, comprising:
    a liquid port;
    a smoothie pod receptacle configured to receive one or more smoothie pods;
    a top structure configured to cover a top portion of the smoothie pod receptacle; and
    a rotatable structure positioned opposite the top structure at a lower portion of the smoothie pod receptacle and having a pod opening and a liquid opening, wherein:
        the rotatable structure is selectively positionable in at least a shielding position, a pod-open position, and a liquid-open position, the shielding position shields the smoothie pod receptacle and the liquid port from the inner area, in the pod-open position, contents of a pod inserted into the smoothie pod receptacle moves to the inner area of the container, and the liquid-open position shields the smoothie pod receptacle from the inner area and provides a channel from the liquid port, through the liquid opening, and to the inner area.

16. The cap of claim 15 wherein the rotatable structure is only selectively positionable from (a) the shielding position to the pod-open position, (b) the pod-open position to the liquid-open position, and (c) the liquid-open position to the shielding position.

17. The cap of claim 15 wherein the shielding position is a first shielding position, and further comprising a second shielding position that shields the smoothie pod receptacle and the liquid port from the inner area.

18. The cap of claim 17 wherein the rotatable structure is only selectively positionable from (a) the first shielding position to the pod-open position, (b) the pod-open position to the second shielding position, (c) the second shielding position to the liquid-open position, and (d) the liquid-open position to the first shielding position.

* * * * *